United States Patent
DiFoggio et al.

(10) Patent No.: US 7,317,989 B2
(45) Date of Patent: *Jan. 8, 2008

(54) METHOD AND APPARATUS FOR CHEMOMETRIC ESTIMATIONS OF FLUID DENSITY, VISCOSITY, DIELECTRIC CONSTANT, AND RESISTIVITY FROM MECHANICAL RESONATOR DATA

(75) Inventors: Rocco DiFoggio, Houston, TX (US); Peter Reittinger, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 66 days.

This patent is subject to a terminal disclaimer.

(21) Appl. No.: 10/801,267

(22) Filed: Mar. 16, 2004

(65) Prior Publication Data

US 2004/0236512 A1  Nov. 25, 2004

Related U.S. Application Data

(63) Continuation-in-part of application No. 10/144,965, filed on May 14, 2002, now Pat. No. 6,938,470.

(60) Provisional application No. 60/291,136, filed on May 15, 2001.

(51) Int. Cl.
*G01H 3/04* (2006.01)
*G01H 3/14* (2006.01)

(52) U.S. Cl. ............ 702/6; 73/152.24; 73/152.58; 73/24.06; 73/61.62; 73/152.14; 73/152.16; 73/152.47; 73/152.52; 166/264; 175/40; 175/48; 175/56; 367/27; 367/81

(58) Field of Classification Search .......... 702/6; 73/152.24, 152.52, 152.14, 152.16; 367/27, 367/81
See application file for complete search history.

(56) References Cited

U.S. PATENT DOCUMENTS 3,130,808 A   4/1964   Walker, Jr. et al.

(Continued)

FOREIGN PATENT DOCUMENTS

EP   0 282 251 B1   2/1993
WO   WO 02/099414   12/2002

OTHER PUBLICATIONS

Webster's Ninth New Collegiate Dicionary, p. 1004.*

(Continued)

*Primary Examiner*—John Barlow
*Assistant Examiner*—Sujoy Kundu
(74) *Attorney, Agent, or Firm*—Bracewell & Giuliani LLP

(57) ABSTRACT

The present invention provides a chemometric equation to estimate fluid density, viscosity, dielectric constant and resistivity for a formation fluid sample downhole. The chemometric estimates can be used directly as estimated values for fluid density, viscosity, dielectric constant and resistivity for a formation fluid sample downhole. The chemometric estimates can also be plugged into a Levenberg-Marquardt (LM) non-linear least squares fit, as an initial estimate of the parameter to be estimated by the LM fit. If the initial parameter estimate is too far from the actual parameter values, the LM algorithm may take a long time to converge or even fail to converge entirely. The present invention estimates an initial value of a parameter that provides a high probability that the LM algorithm will converge to a global minimum.

25 Claims, 19 Drawing Sheets

U.S. PATENT DOCUMENTS

| | | | |
|---|---|---|---|
| 3,346,058 A | 10/1967 | Bouyoucos | |
| 3,390,737 A | 7/1968 | Johnson | |
| 3,449,940 A | 6/1969 | Banks | |
| 3,608,715 A | 9/1971 | Snyder et al. | |
| 3,760,204 A | 9/1973 | Yester, Jr. | |
| 3,835,288 A | 9/1974 | Henderson | |
| 3,903,732 A | 9/1975 | Rork et al. | |
| 4,526,480 A | 7/1985 | Ward | |
| 4,574,639 A | 3/1986 | Ward | |
| 4,602,505 A | 7/1986 | Kanda et al. | |
| 4,679,427 A | 7/1987 | Kanda et al. | |
| 4,729,237 A | 3/1988 | Suzuki et al. | |
| 4,922,745 A | 5/1990 | Rudkin et al. | |
| 5,006,845 A | 4/1991 | Calcar et al. | |
| 5,048,351 A | 9/1991 | Dames | |
| 5,204,529 A | 4/1993 | Diatschenko | |
| 5,269,188 A | 12/1993 | Esin et al. | |
| 5,329,811 A | 7/1994 | Schultz et al. | |
| 5,361,632 A | 11/1994 | Magnani | |
| 5,622,223 A | 4/1997 | Vasquez | |
| 5,662,166 A | 9/1997 | Shammai | |
| 5,734,098 A | 3/1998 | Kraus et al. | |
| 5,741,962 A * | 4/1998 | Birchak et al. | 73/152.16 |
| 5,763,781 A * | 6/1998 | Netzer | 73/504.16 |
| 5,798,982 A * | 8/1998 | He et al. | 367/73 |
| 5,837,893 A | 11/1998 | Chu | |
| 6,073,492 A | 6/2000 | Rosselson et al. | |
| 6,128,949 A | 10/2000 | Kleinberg | |
| 6,176,323 B1 | 1/2001 | Weirich et al. | |
| 6,182,499 B1 * | 2/2001 | McFarland et al. | 73/24.06 |
| 6,336,353 B2 | 1/2002 | Matsiev et al. | |
| 6,346,813 B1 * | 2/2002 | Kleinberg | 324/303 |
| 6,357,536 B1 | 3/2002 | Schrader et al. | |
| 6,378,364 B1 | 4/2002 | Pelletier et al. | |
| 6,393,895 B1 | 5/2002 | Matsiev et al. | |
| 6,401,519 B1 | 6/2002 | McFarland et al. | |
| 6,412,354 B1 | 7/2002 | Birchak et al. | |
| 6,494,079 B1 * | 12/2002 | Matsiev et al. | 73/24.05 |
| 6,938,470 B2 * | 9/2005 | DiFoggio et al. | 73/152.24 |
| 7,162,918 B2 * | 1/2007 | DiFoggio et al. | 73/152.32 |
| 2002/0088284 A1 | 7/2002 | Takeuchi et al. | |
| 2003/0041653 A1 | 3/2003 | Matsiev et al. | |

OTHER PUBLICATIONS

SINIMS Oil and Gas Workshop, DRAFT: Notes of Presentations and Discussions ICMS, Edinburgh, Mar. 11, 2002; pp. 1-9.

Alan Fleming, Theory of the Vibrating Tuning Fork Fluid Density Tool, Mar. 15, 2002, http://www.lancs.ac.uk/dcpts/spc/conf/csgi/NanGall/transducer.htm, 1 page.

Solartron 7826 Insertion Liquid Density Transducer, http://www.mobrey.com/products/density/7826.php, 2 pages, retrieved Mar. 29, 2006.

* cited by examiner

CREATE SYNTHETIC DATA SET BY EXPERIMENTAL DESIGN USING SEVERAL VALUES OF EACH PROPERTY — 610

CREATE CHEMOMETRIC EQUATIONS THAT CORRELATE FLUID PROPERTIES TO IMPEDANCE VS. FREQUENCY — 620

APPLY THESE EQUATIONS TO MEASURED RESONATOR RESPONSE SO AS TO ESTIMATE FLUID PROPERTIES — 630

ALTERNATIVELY, USE CHEMOMETRIC ESTIMATES AS STARTING VALUES IN NON-LINEAR LEAST-SQUARE FIT — 640

*FIG. 6*

Density
Regression Summary for Dependent Variable: g/cc (Synthetic Impedance Data.sta)
R= .99263581  R² = .98532585  Adjusted R² = .98514010
F(1,79)=5304.6 p<0.0000 Std. Error of estimate: .05053

|  | Beta | Std. Err. | B | Std. Err. | t(79) | p-level |
|---|---|---|---|---|---|---|
| Intercept |  |  | -10.0370 | 0.151558 | -66.2254 | 0.00E+00 |
| 1/FLZD1 | 0.992636 | 0.013629 | 32.4538 | 0.445593 | 72.8328 | 0.00E+00 |

Density
*Regression Summary for Dependent Variable: g/cc (Synthetic Impedance Data.sta)*
$R = .99970856$  $R^2 = .99941721$  Adjusted $R^2 = .99933396$
$F(10,70) = 12004.$ $p < 0.0000$ Std. Error of estimate: .01070

|  | Beta | Std. Err. | B | Std. Err. | t(70) | p-level |
|---|---|---|---|---|---|---|
| Intercept |  |  | -10.1349 | 0.04869 | -208.130 | 0.000000E+00 |
| log(MaxD2) | 0.086694 | 0.006457 | 0.0309 | 0.00230 | 13.426 | 4.807740E-21 |
| 1/Min_D2 | 0.117544 | 0.009139 | 0.0000 | 0.00000 | 12.862 | 4.117729E-20 |
| 1/Max_D1 | 0.052427 | 0.006022 | 0.0000 | 0.00000 | 8.706 | 9.173387E-13 |
| AvgD1 | -0.047915 | 0.006490 | -93.3906 | 12.64923 | -7.383 | 2.489016E-10 |
| 1/FMn_D2 | 0.447306 | 0.082745 | 13.8455 | 2.56121 | 5.406 | 8.448959E-07 |
| 1/FMn_D1 | 0.446249 | 0.086245 | 14.5310 | 2.80834 | 5.174 | 2.086349E-06 |
| 1/Max | 0.438247 | 0.106496 | 0.0261 | 0.00633 | 4.115 | 1.041422E-04 |
| 1/Min | -0.432207 | 0.108163 | -0.0218 | 0.00547 | -3.996 | 1.573313E-04 |
| 1/FLZD1 | 0.186323 | 0.047327 | 5.8908 | 1.49630 | 3.937 | 1.924973E-04 |
| Log(Max) | 0.071356 | 0.018739 | 0.1189 | 0.03122 | 3.808 | 2.976181E-04 |

Viscosity

Regression Summary for Dependent Variable: cPs (Synthetic Impedance Data.sta)
$R = .97696409$ $R^2 = .95445882$ Adjusted $R^2 = .95206192$
$F(4,76) = 398.2$ $p < 0.0000$ Std. Error of estimate: .26970

|  | Beta | Std. Err. | B | Std. Err. | t(76) | p-level |
|---|---|---|---|---|---|---|
| Intercept |  |  | -15.694 | 0.9671 | -16.2279 | 2.089853E-26 |
| 1/MinD2 | -0.840896 | 0.035160 | 0.000 | 0.0000 | -23.9160 | 4.151239E-37 |
| FreqRMaxD1 | 0.506923 | 0.028371 | 5.662 | 0.3169 | 17.8679 | 6.229948E-29 |
| MinD2 | 0.376456 | 0.033230 | 8268.363 | 729.8467 | 11.3289 | 5.432749E-18 |
| Sqr_Min | -0.117944 | 0.024612 | -10.112 | 2.1102 | -4.7922 | 7.999455E-06 |

Viscosity
Regression Summary for Dependent Variable: cPs (Synthetic Impedance Data.sta)
$R = .97873578$ $R^2 = .95792372$ Adjusted $R^2 = .95511863$
$F(5,75) = 341.5$ $p < 0.0000$ Std. Error of estimate: .26096

|  | Beta | Std. Err. | B | Std. Err. | t(75) | p-level |
|---|---|---|---|---|---|---|
| Intercept |  |  | -17.653 | 1.214 | -14.5445 | 1.57E-23 |
| FreqLZeroD1 | 0.483355 | 0.029189 | 5.411 | 0.327 | 16.5596 | 9.17E-27 |
| 1/MinD2 | -0.693825 | 0.058609 | 0.000 | 0.000 | -11.8381 | 7.78E-19 |
| Cub_Min | -0.169016 | 0.031429 | -69.316 | 12.890 | -5.3776 | 8.24E-07 |
| MinD2 | 0.245608 | 0.065284 | 5394.464 | 1433.871 | 3.7622 | 3.32E-04 |
| log(MaxD2) | -0.268470 | 0.097688 | -0.284 | 0.103 | -2.7482 | 7.50E-03 |

Viscosity

Regression Summary for Dependent Variable: cPs (Synthetic Impedance Data.sta)
$R = .98468409$ $R^2 = .96960276$ Adjusted $R^2 = .96757627$
$F_{(5,75)} = 478.47$ $p < 0.0000$ Std. Error of estimate: .22181

|  | Beta | Std. Err. | B | Std. Err. | t(75) | p-level |
|---|---|---|---|---|---|---|
| Intercept |  |  | -12.938 | 0.8918 | -14.5075 | 1.813627E-23 |
| 1/MinD2 | -0.691176 | 0.043747 | 0.000 | 0.0000 | -15.7994 | 1.434065E-25 |
| PK | 0.368418 | 0.029871 | 250.435 | 20.3047 | 12.3338 | 1.005152E-19 |
| log(MaxD2) | -0.368199 | 0.043609 | -0.390 | 0.0462 | -8.4431 | 1.709891E-12 |
| Cub_Min | -0.131400 | 0.023774 | -53.889 | 9.7499 | -5.5272 | 4.512895E-07 |
| P27_D2 | 0.128036 | 0.028700 | 3078.767 | 690.1188 | 4.4612 | 2.817552E-05 |

Dielectric Constant
Regression Summary for Dependent Variable: Dielectric (Synthetic Impedance Data.sta)
$R = .99511668$  $R^2 = .99025720$  Adjusted $R^2 = .98974442$
$F(4,76) = 1931.2$  $p < 0.0000$  Std. Error of estimate: 1.1857

|  | Beta | Std. Err. | B | Std. Err. | t(76) | p-level |
|---|---|---|---|---|---|---|
| Intercept |  |  | -9.15 | 0.581 | -15.7513 | 1.206053E-25 |
| AvgD1 | 1.37132 | 0.054288 | 75492.69 | 2988.616 | 25.2601 | 1.029444E-38 |
| Sqr_Max | -1.46607 | 0.108461 | -1157.11 | 85.604 | -13.5170 | 6.567799E-22 |
| Cub_Avg | 4.64294 | 0.680918 | 17514.38 | 2568.600 | 6.8187 | 1.924593E-09 |
| Cub_Max | 2.46760 | 0.623626 | -8978.25 | 2269.034 | -3.9589 | 1.693159E-04 |

Dielectric Constant
Regression Summary for Dependent Variable: Dielectric (Synthetic Impedance Data.sta)
R= .99901744 R² = .99803585 Adjusted R² = .99795932
F(3,77)=13042. p<0.0000 Std. Error of estimate: .52890

|  | Beta | Std. Err. | B | Std. Err. | t(77) | p-level |
|---|---|---|---|---|---|---|
| Intercept |  |  | 35.64 | 1.2392 | 28.7567 | 6.24E-43 |
| Cub_Min | 0.676927 | 0.005494 | 2638.71 | 21.4159 | 123.2124 | 0.00E+00 |
| AvgD1 | 0.656755 | 0.010915 | 36155.19 | 600.9014 | 60.1683 | 0.00E+00 |
| Log(AvgD1) | 0.401660 | 0.011145 | 10.63 | 0.2950 | 36.0399 | 0.00E+00 |

Conductivity
Regression Summary for Dependent Variable: 1/ohm*m (Synthetic Impedance Data.sta)
$R = .99825839$ $R^2 = .99651982$ Adjusted $R^2 = .99633665$
$F(3,77) = 13042.$ $p<0.0000$ Std. Error of estimate: .52890

|  | Beta | Std. Err. | B | Std. Err. | t(76) | p-level |
|---|---|---|---|---|---|---|
| Intercept |  |  | 0.000112 | 0.000025 | 4.3989 | 3.495104E-05 |
| Max | -3.84661 | 0.091676 | -0.002934 | 0.000070 | -41.9589 | 0.000000E+00 |
| Min | 3.86666 | 0.064796 | 0.002932 | 0.000123 | 23.9154 | 4.158121E-37 |
| Cub_Min | 0.47895 | 0.011145 | 0.007172 | 0.000970 | 7.3916 | 1.594179E-10 |
| Log(Min) | 0.37400 | 0.089062 | 0.000063 | 0.000015 | 4.1993 | 7.204409E-05 |

| Some Definitions of Variables | |
|---|---|
| Min | Minimum Impedance in Spectrum |
| Max | Maximum Impedance in Spectrum |
| Avg | Average Impedance in Spectrum |
| PK | Frequency of 1st Derivative Minimum Value (an inverted PeaK) |
| Sqr_ | Square_of_ |
| Cub_ | Cube_of_ |
| Log( ) | Log 10 of |
| 1/ | Reciprocal of |
| D1 | First Derivative of Impedance vs Frequency |
| D2 | Second Derivative of Impedance vs Frequency |
| D3 | Third Derivative of Impedance vs Frequency |
| MinD1= | Minimum of First Derivative of Impedance in Spectrum |
| MaxD1= | Maximum of First Derivative of Impedance in Spectrum |
| MinD2= | Minimum of Second Derivative of Impedance in Spectrum |
| MaxD2= | Maximum of Second Derivative of Impedance in Spectrum |
| 1/FMn_D1 | Reciprocal of Frequency of Minimum D1 (Inverted Peak) |
| 1/FMx_D1 | Reciprocal of Frequency of Minimum D1 |
| FreqAtMinD1 | Frequency of Minimum D1 (Inverted Peak) |
| FreqAtMaxD1 | Frequency of Minimum D1 (May pick up small bump on either side of Inverted Peak) |
| FreqAtMinD2 | Frequency of Minimum D2 |
| FreqAtMaxD2 | Frequency of Maximum D2 |
| FreqAtMinD3 | Frequency of Minimum D3 |
| FreqAtMaxD3 | Frequency of Maximum D3 |
| FreqLMaxD1= | Frequency of LEFT Maximum D1 (Left of Inverted Peak) |
| FreqRMaxD1= | Frequency of RIGHT Maximum D1 (Left of Inverted Peak) |
| FreqLZeroD1=FLZD1 = | Frequency of LEFT Zero D1 (Left X-axis Crossing Point) |
| FreqRZeroD1=FLZD1 = | Frequency of RIGHT Zero D1 (Right X-axis Crossing Point) |

FIG. 8E

000
METHOD AND APPARATUS FOR CHEMOMETRIC ESTIMATIONS OF FLUID DENSITY, VISCOSITY, DIELECTRIC CONSTANT, AND RESISTIVITY FROM MECHANICAL RESONATOR DATA

CROSS REFERENCE TO RELATED APPLICATIONS

The patent application is a continuation in part and claims priority from U.S. patent application Ser. No. 10/144,965 filed on May 14, 2002 now U.S. Pat. No. 6,938,470 entitled "Method and Apparatus for Downhole Fluid Characterization Using Flexural Mechanical Resonators" by Rocco DiFoggio which is incorporated herein by reference and claims priority from U.S. patent application Ser. No. 60/291,136 filed on May 15, 2001 entitled "Method and Apparatus for Downhole Fluid Characterization Using Flexural Mechanical Resonators" by Rocco DiFoggio.

BACKGROUND OF THE INVENTION

1. Field of the Invention

The present invention relates to the field of downhole fluid analysis in hydrocarbon producing wells. More particularly, the present invention relates to a method and apparatus for using a chemometric equation to estimate fluid density, viscosity, dielectric constant, and resisitivity from flexural mechanical resonator data obtained downhole in a borehole during monitoring while drilling or during wireline operations.

2. Background of the Related Art

There is considerable interest in measuring density, viscosity, dielectric constant, resistivity and other parameters for formation fluids. It is particularly useful to perform these measurements downhole at reservoir conditions of high temperature and high pressure during formation sampling, producing or drilling operations. Numerous technologies have been employed toward the end of measuring fluid parameters such as viscosity downhole. U.S. Pat. No. 6,182,499 discusses systems and methods for characterization of materials and combinatorial libraries with mechanical oscillators. U.S. Pat. No. 5,734,098 (the '098 patent) discusses a method for monitoring and controlling chemical treatment of petroleum, petrochemical and processes with on-line quartz crystal microbalance sensors. The '098 patent invention utilizes thickness shear mode (TSM) resonators, which simultaneously measure mass deposition and fluid properties such as viscosity and or density of a fluid. U.S. Pat. No. 6,176,323 (the '323 patent) discloses drilling systems with sensors for determining properties of drilling fluid downhole. The '323 patent discloses a plurality of pressure sensors positioned at different depths to determine a fluid gradient. U.S. Pat. No. 5,741,962 (the '962 patent) discloses a method and apparatus for analyzing a formation fluid using acoustic measurements.

The '962 patent invention acoustically determines density and compressibility from acoustic impedance and sound speed. U.S. Pat. No. 5,622,223 (the '223 patent) discloses a method and apparatus for characterizing formation fluid samples utilizing differential pressure measurements. The '223 patent discloses an apparatus that provides two pressure gauges at different depths to determine density from a fluid pressure gradient. U.S. Pat. No. 5,006,845 describes an invention that uses differential fluid pressure at two depths to determine fluid density. U.S. Pat. No. 5,361,632 discloses a method and apparatus for determining multiphase hold up fractions using a gradiometer and a densiometer to provide a pressure gradient to determine fluid density. U.S. Pat. No. 5,204,529 discloses a method and apparatus for measuring borehole fluid density, formation density and or borehole diameter using back-scattered gamma radiation to determine fluid density.

Flexural mechanical resonators have been used in the laboratory for rapid characterization of large numbers of fluid samples. See L. F. Matsiev, Application of Flexural Mechanical Resonator to High Throughput Liquid Characterization, 2000 IEEE International Ultrasonics Symposium, Oct. 22-25, 2000 San Juan, Puerto Rico, incorporated herein by reference in its entirety; L. F. Matsiev, Application of Flexural Mechanical Resonator to High Throughput Liquid Characterization, 1999 IEEE International Ultrasonics Symposium, Oct. 17-20, Lake Tahoe, Nevada, incorporated herein by reference in its entirety; L. F. Matsiev, Application of Flexural Mechanical Resonator to High Throughput Liquid Characterization, 1998 IEEE International Ultrasonics Symposium, Oct. 5-8, 1998, Sendai, Miyagi, Japan, incorporated herein by reference in its entirety.

The use of mechanical resonators are described in U.S. Pat. No. 6,455,316 B1 which is incorporated herein by reference in its entirety; U.S. Pat. No. 6,393,895 B1 which is incorporated herein by reference in its entirety; U.S. Pat. No. 6,336,353 B2 which is incorporated herein by reference in its entirety; U.S. patent Publication No. 2003/0041653 A1 which is incorporated herein by reference in its entirety; U.S. patent Publication No. 2003/0000291 A1 which is incorporated herein by reference in its entirety; U.S. Pat. No. 6,401,591 B2 which is incorporated herein by reference in its entirety; and U.S. Pat. No. 6,6,528,026 B2 which is incorporated herein by reference in its entirety.

An example of a method and apparatus for determining down fluid characteristics using flexural mechanical resonators is described in the parent application, U.S. patent application Ser. No. 10/144,965 filed on May 14, 2002 entitled "Method and Apparatus for Downhole Fluid Characterization Using Flexural Mechanical Resonators." (the '965 patent application). The '965 patent application describes a method or apparatus utilizing a flexural mechanical resonator to determine density, viscosity or other fluid properties in a downhole environment. An example of a suitable algorithm for use in association with the method and apparatus described in the '965 patent application is a Levenberg-Marquardt (LM) non-linear least squares fit. The LM fit uses an initial estimate for determination of a fluid parameter. If the initial parameter estimate is too far from the actual parameter values, the LM algorithm may take a long time to converge or fail to converge at all. Thus, there is a need for a method and apparatus for accurately estimating the initial parameter inputs for the LM algorithm in determining fluid parameters.

SUMMARY OF THE INVENTION

The present invention provides chemometric equations to estimate fluid properties such as density, viscosity, dielectric constant and resistivity for a formation fluid sample in real time downhole from impedance-versus-frequency data of a mechanical resonator immersed in the fluid. These chemometric estimates can be used directly as estimates of fluid density, viscosity, dielectric constant and resistivity for a downhole formation fluid sample. The chemometric estimates also can be used as initial estimates of these parameters in a Levenberg-Marquardt (LM) iterative non-linear least squares fit of the theoretical model to the measured data. Good initial estimates are important to LM fits because, if the initial parameter estimates are too far from the actual parameter values, the LM algorithm may take a long time to converge or may fail to converge at all. The present invention provides an initial estimate of a parameter to the LM algorithm that results in a high probability that the LM algorithm will converge to a proper global minimum.

BRIEF DESCRIPTION OF THE DRAWINGS

FIG. 6 is a flow chart of functions performed in an example of the present invention;

DETAILED DESCRIPTION OF AN EXEMPLARY EMBODIMENT

Figure 1:
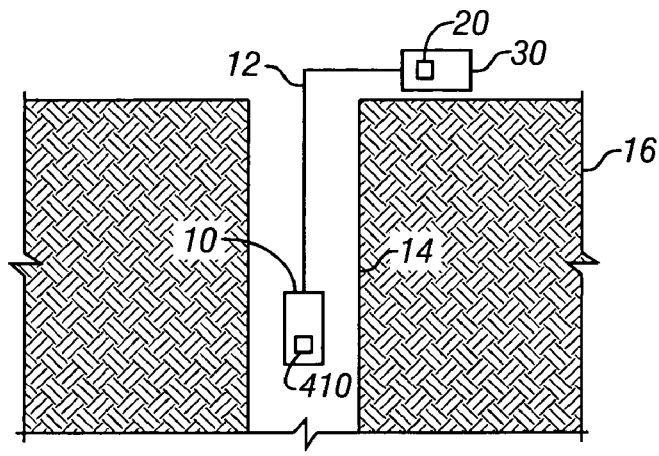
FIG. 1 is a schematic diagram of a exemplary embodiment of the present invention deployed on a wireline in a downhole environment.

The present invention provides a chemometric equation to estimate fluid density, viscosity, dielectric constant, and resistivity for a formation fluid sample downhole from the impedance-versus-frequency data of a mechanical resonator. The chemometric estimates can be used directly or as initial parameter estimates in a Levenberg-Marquardt (LM) non-linear least squares fit of the theoretical model to the measured data. Good initial estimates are important to LM fits because, if the initial parameter estimate is too far from the actual parameter values, the LM algorithm may take a long time to converge or fail to converge at all.

The parent '965 patent application describes a downhole method and apparatus using a mechanical resonator, for example, a tuning fork to provide real-time direct measurements and estimates of the viscosity, density and dielectric constant for formation fluid or filtrate in a hydrocarbon producing well.

The present invention enhances the implementation of a resonating tuning fork downhole used to estimate fluid density, viscosity, dielectric constant and resistivity. Mechanical resonators respond to the product of the density and viscosity of a fluid into which they are immersed. Symyx Technologies Incorporated of Santa Clara, Calif. has developed a model for a miniature tuning fork resonator, which, in combination with a non-linear least squares fit, enables separate determination of density and viscosity of fluid, rather than merely the product of these two properties. Prior resonators could only determine the product of density and viscosity and thus viscosity or density could not be independently determined. The present invention provides a tuning fork or flexural resonator, which is excited, monitored and its response processed using a chemometric equation or the combination of a chemometric equation and a LM non-linear least squares fit. The processing determines not only the density and viscosity of a fluid, but also the dielectric constant, resistivity and other parameters of a fluid downhole.

The present example of the invention is implemented using a resonating tuning fork downhole to estimate fluid density, viscosity, dielectric constant, and resistivity. The present invention measures the impedance versus frequency (impedance spectrum) for a flexural mechanical resonator in the vicinity of its resonant frequency. To convert this direct measurement to density, viscosity, dielectric constant and resistivity, the present invention determines a best fit between a theoretical spectrum and the measured impedance spectrum for the resonator, e.g., tuning fork, using a Levenberg-Marquardt (LM) nonlinear least squares fit algorithm. The fitting parameters provide density, viscosity, dielectric constant and resistivity values. If the initial parameter value estimates for the fitting parameters are too far from the actual parameter values, the LM fitting algorithm may take a long time to converge or may fail to converge entirely. Even if the LM algorithm does converge, it may converge to a local minimum rather than a global minimum. When logging a well in real time, the operator does not want to wait a long time for an answer nor does the operator want the algorithm to converge to the wrong answer at a local minimum rather than a global minimum.

The present invention computes a result quickly, uses less computing resources and thus provides more useful and accurate initial estimates for the LM fitting parameters. The initial estimates provided by the present invention are robust, they do not require iteration, and they are quickly computed. The present invention uses chemometrics to obtain the initial estimates of fitting parameters. These chemometric estimations can then be used directly as estimates of a fluid parameter value or property or provided to the LM algorithm. The chemometric estimations provided to the LM algorithm provide a high probability of allowing the LM algorithm to converge quickly to the correct global minimum for the fluid parameter value estimation.

Traditional chemometrics can be defined as multiple linear regressions (MLR), principle components regressions (PCR), or partial least squares (PLS). Chemometrics can be applied either to an original data set or to a preprocessed version of the original data such as a Savitzky-Golay (SG) smoothed curve or its derivatives. When using these traditional chemometric techniques, the property-prediction equation is usually just an offset constant plus the dot product of a weights vector with the measured resonator impedance spectrum. This is a straightforward calculation that requires a relatively small amount of computer time as the calculation is non-iterative. However, chemometric equations can also be based on minimum, maximum, or zero-crossing values or other similarly derived properties of the data. In some cases, the chemometric predictions or the fits to the synthetic data are sufficiently accurate to use directly without going to the second step of applying a LM fitting algorithm.

Figure 2:
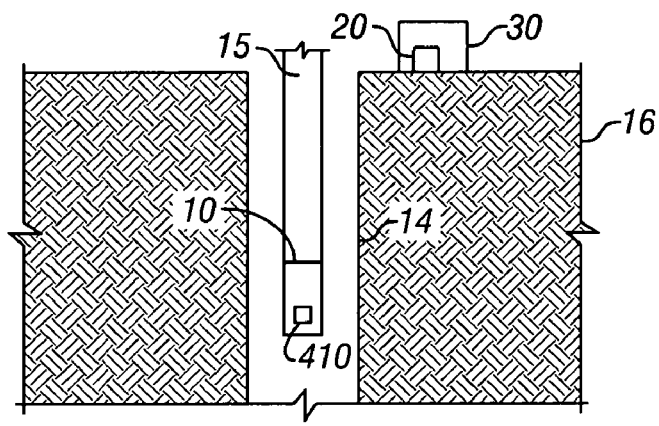
FIG. 2 is a schematic diagram of an exemplary embodiment of the present invention deployed on a drill string in a monitoring while drilling environment.
Figure 3:
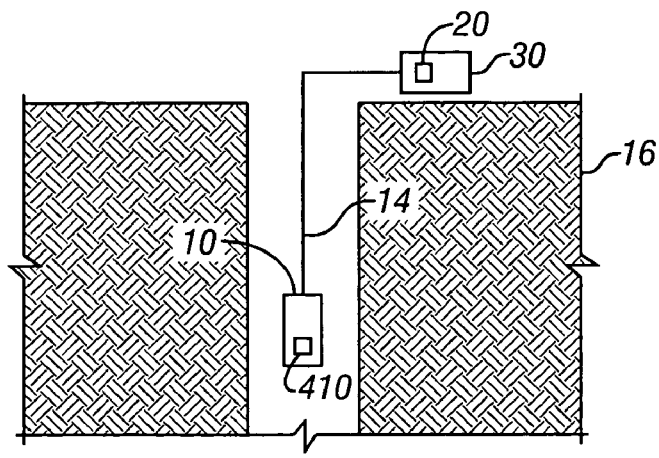
FIG. 3 is a schematic diagram of a exemplary embodiment of the present invention deployed on a flexible tubing 13 in a downhole environment.

FIG. 1 is a schematic diagram of an exemplary embodiment of the present invention deployed on a wireline in a downhole environment. As shown in FIG. 1, a downhole tool 10 containing a mechanical resonator assembly 410 is deployed in a borehole 14. The borehole is formed in formation 16. Tool 10 is deployed via a wireline 12. Data from the tool 10 is communicated to the surface to a computer processor 20 with memory inside of an intelligent completion system 30. FIG. 2 is a schematic diagram of a exemplary embodiment of the present invention deployed on a drill string 15 in a monitoring while drilling environment. FIG. 3 is a schematic diagram of an exemplary embodiment of the present invention deployed on a flexible tubing 13 in a downhole environment.

Figure 4:
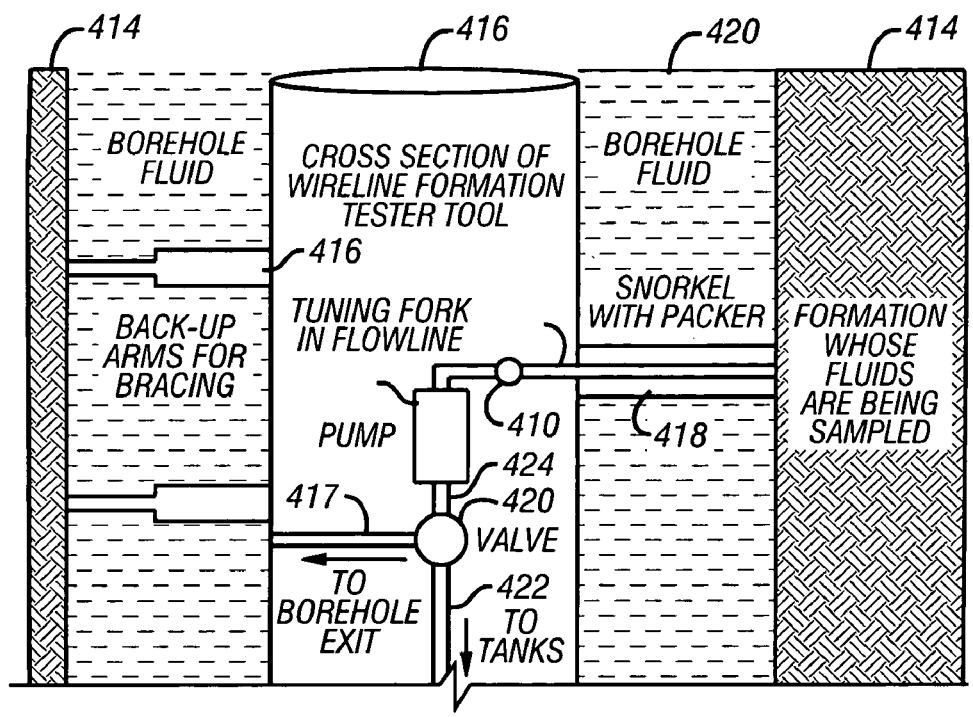
FIG. 4 is a schematic diagram of an exemplary embodiment of the present invention as deployed in a wireline downhole showing a cross section of a wireline formation tester tool.

FIG. 4 is a schematic diagram of an exemplary embodiment of the present invention as deployed from a wireline downhole environment showing a cross section of a wireline formation tester tool. As shown in FIG. 4, the tool 416 is deployed in a borehole 420 filled with borehole fluid. The tool 416 is positioned in the borehole by backup arms 417. A packer with a snorkel 418 contacts the borehole wall for extracting formation fluid from the formation 414. Tool 416 contains mechanical resonator assembly 410 disposed in flow line 426. The mechanical resonator 411 or oscillator, shown in FIG. 5 as a tuning fork is excited by an electric current applied to its electrodes (not shown). The resonator response is monitored to determine density, viscosity, dielectric coefficient and resistivity of the formation fluid. Pump 412 pumps formation fluid from formation 414 into flow line 426. Formation fluid travels through flow line 424 into valve 420, which directs the formation fluid to line 422 to save the fluid in sample tanks or to line 417 where the formation fluid exits to the borehole. The present invention uses the response tuning fork to determine fluid density, viscosity and dielectric coefficient while fluid is pumped by pump 412 or while the fluid is static, that is, when pump 412 is stopped.

Figure 5:
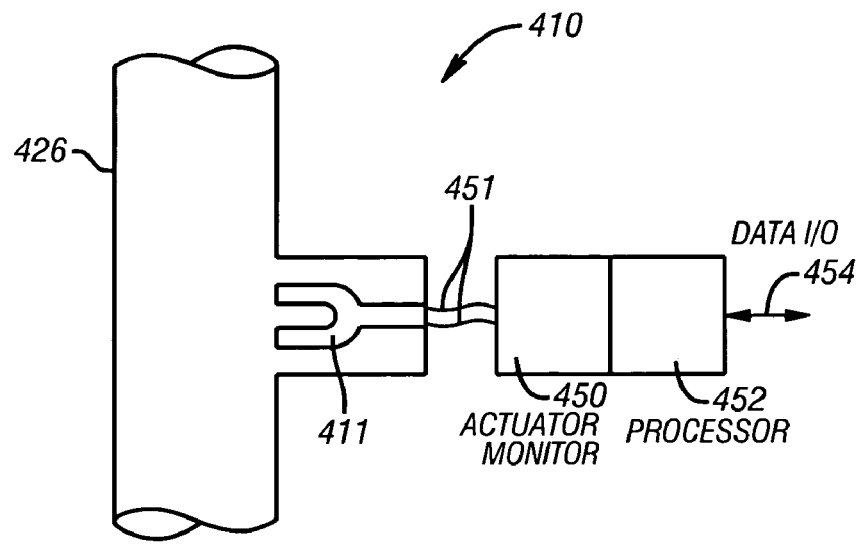
FIG. 5 is an illustration of an example of the present invention showing a flow line and an associated resonator.
Figure 7A:
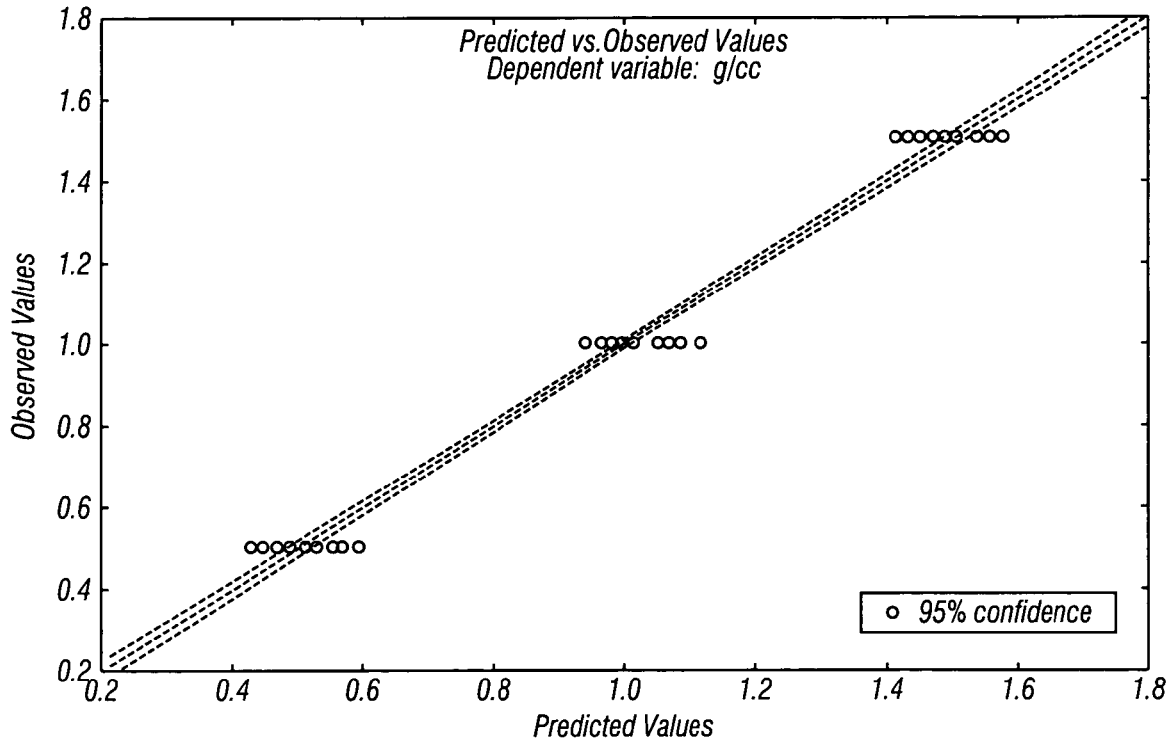
FIG. 7 lists some chemometric correlations to synthetic fluid parameter data.
Figure 7B:
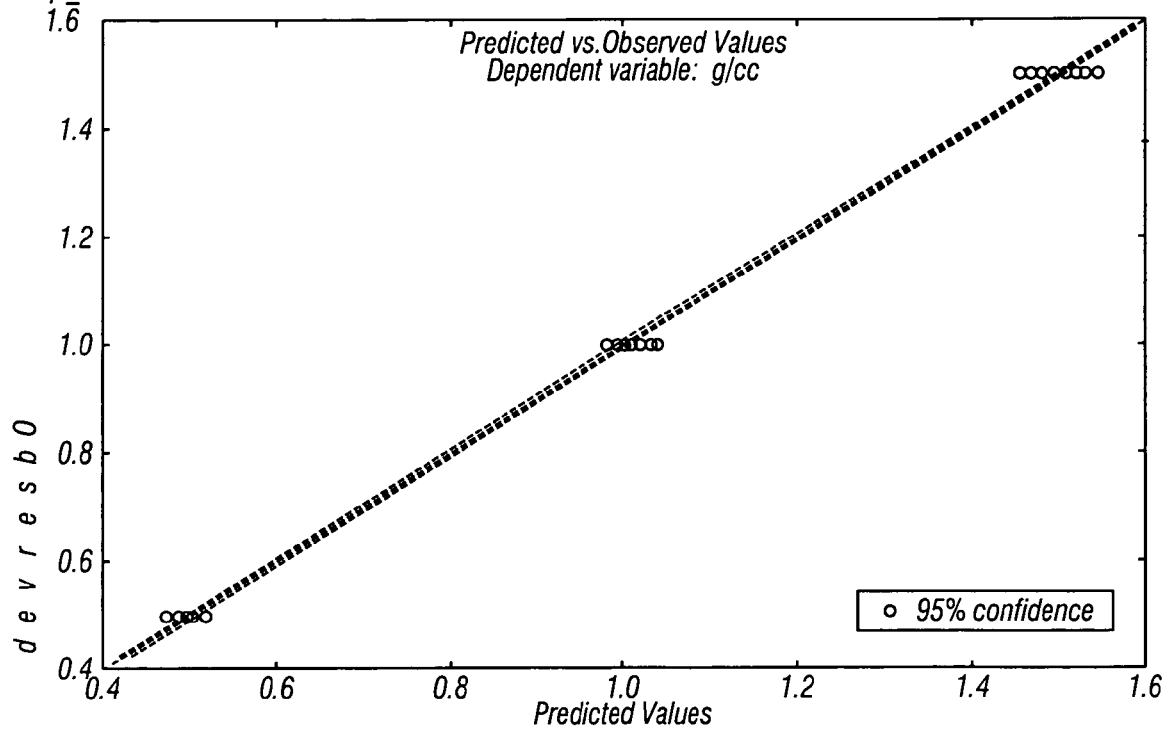
Figure 7C:
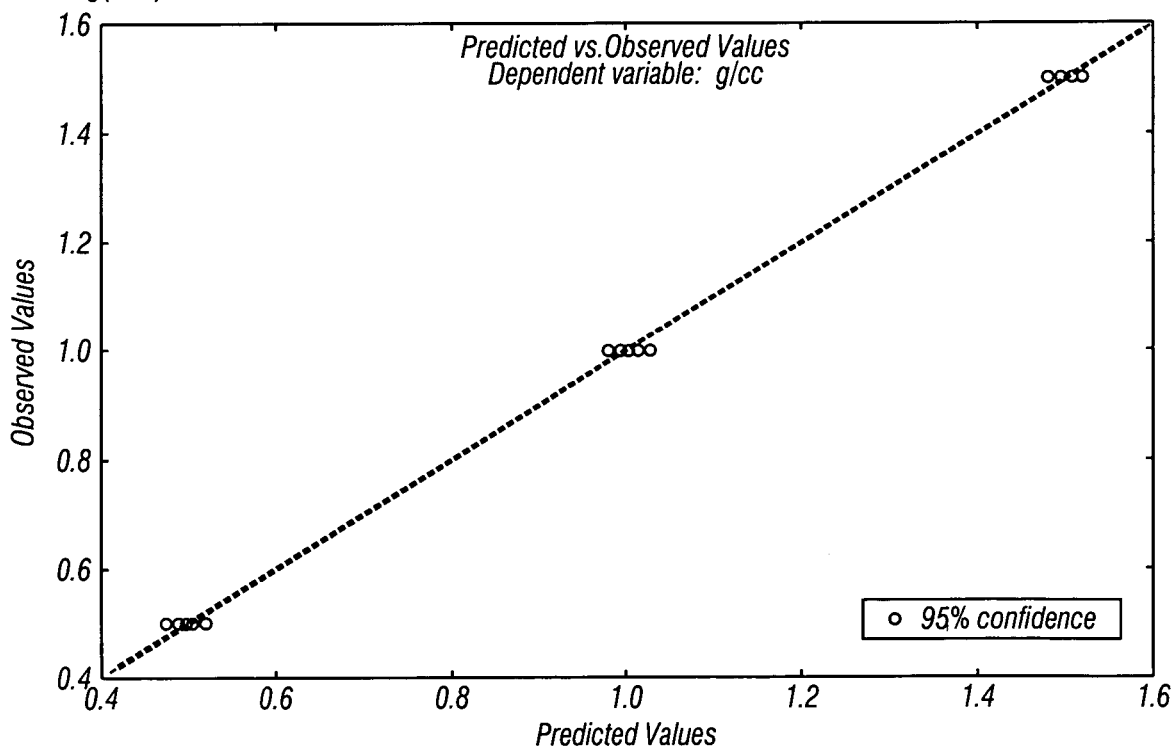
Figure 7D:
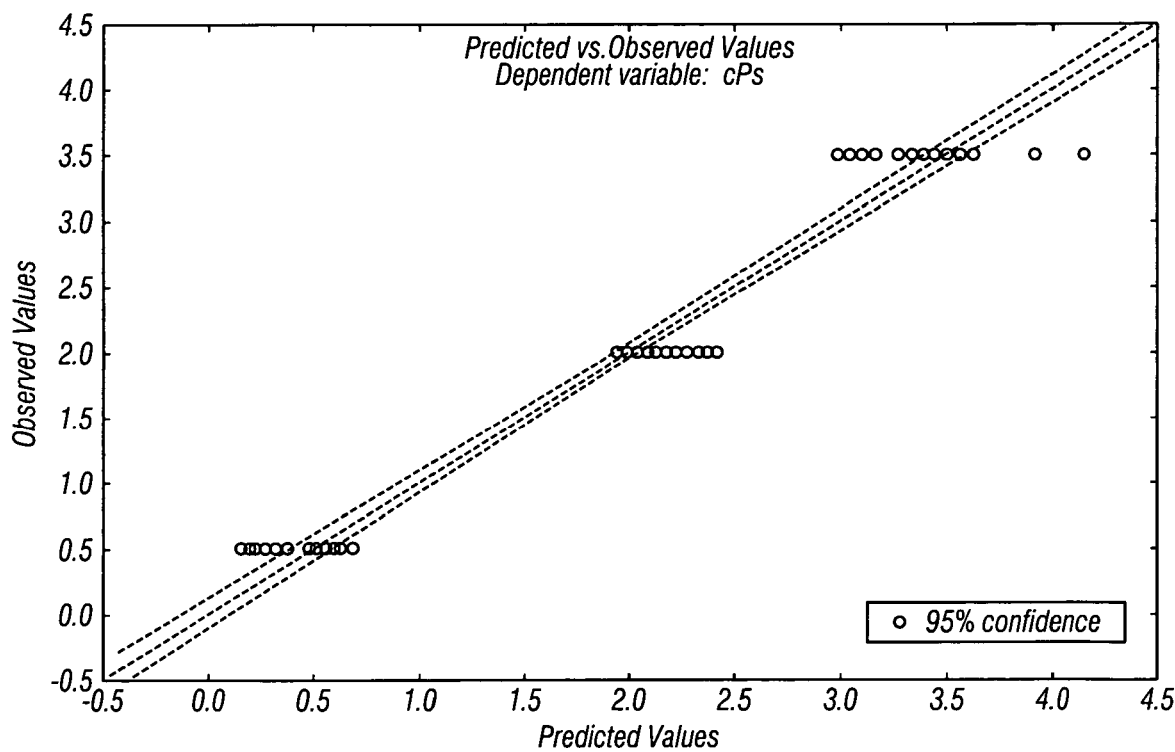
Figure 7E:
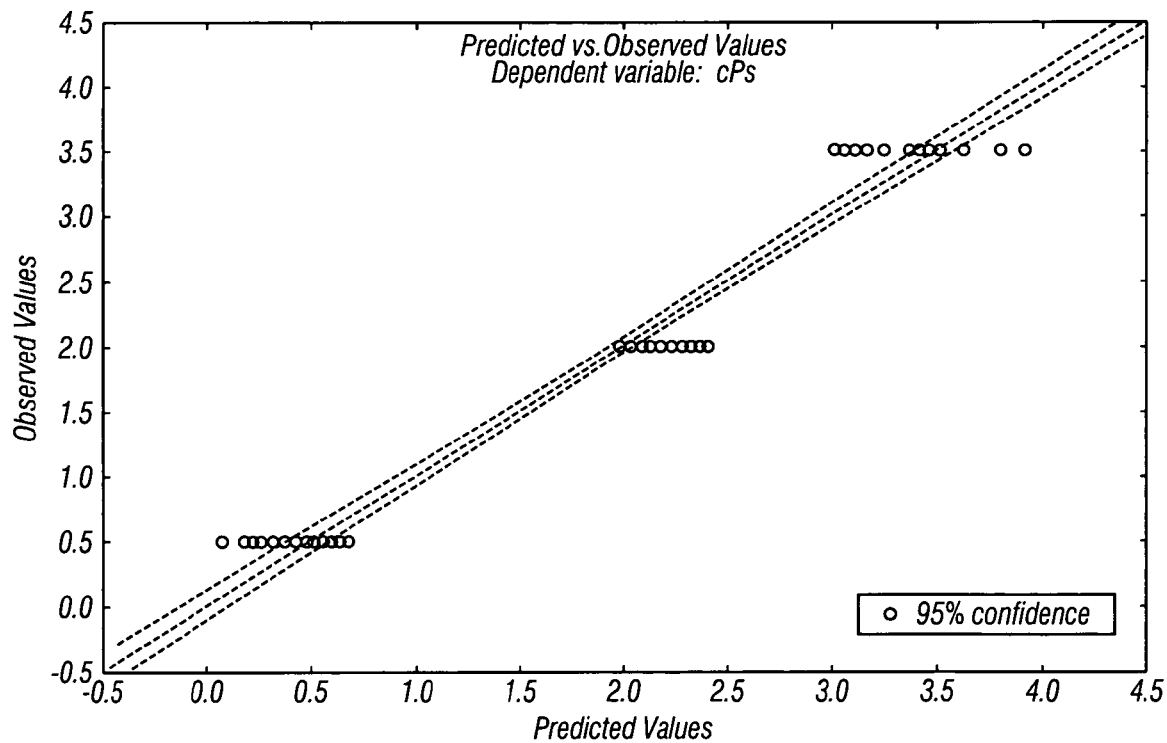
Figure 7F:
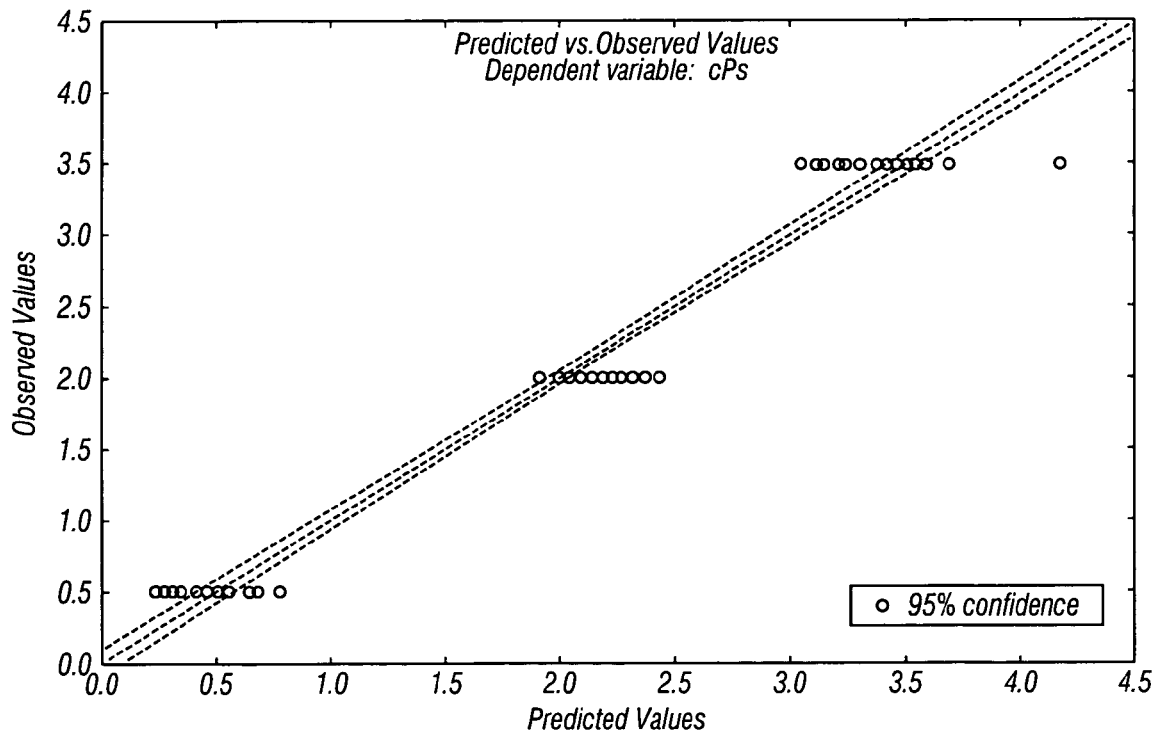
Figure 8A:
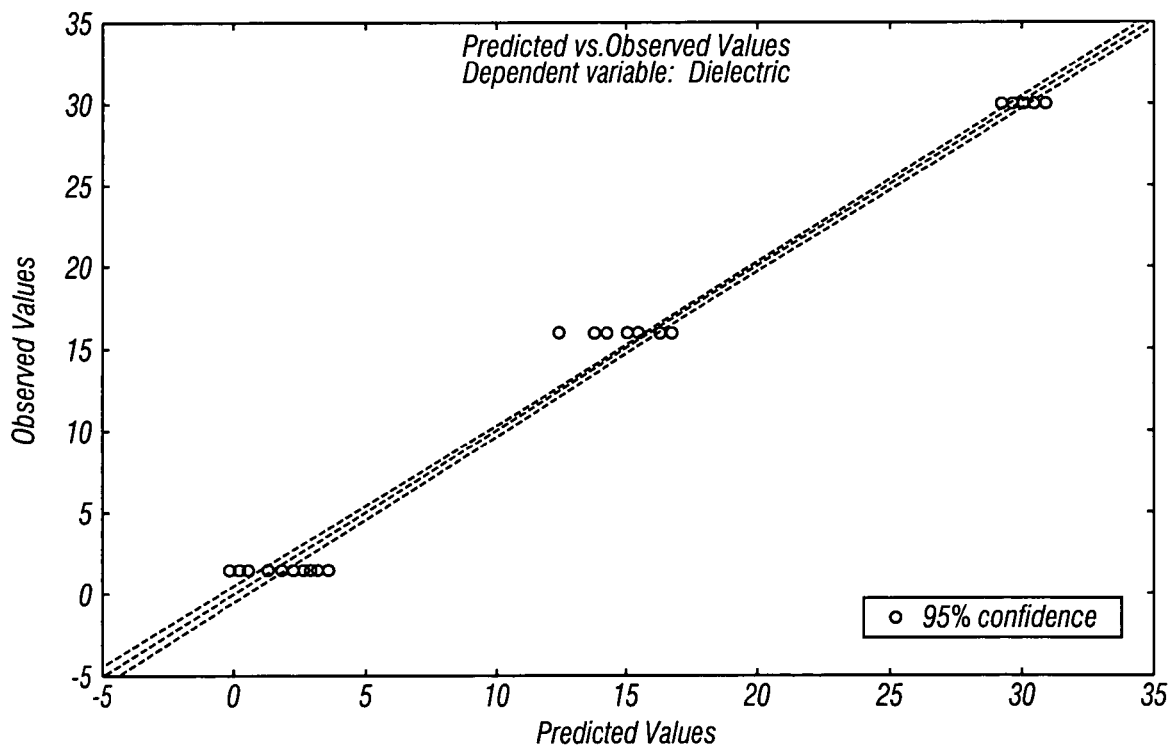
FIG. 8 lists some additional chemometric correlations to synthetic fluid parameter data.
Figure 8B:
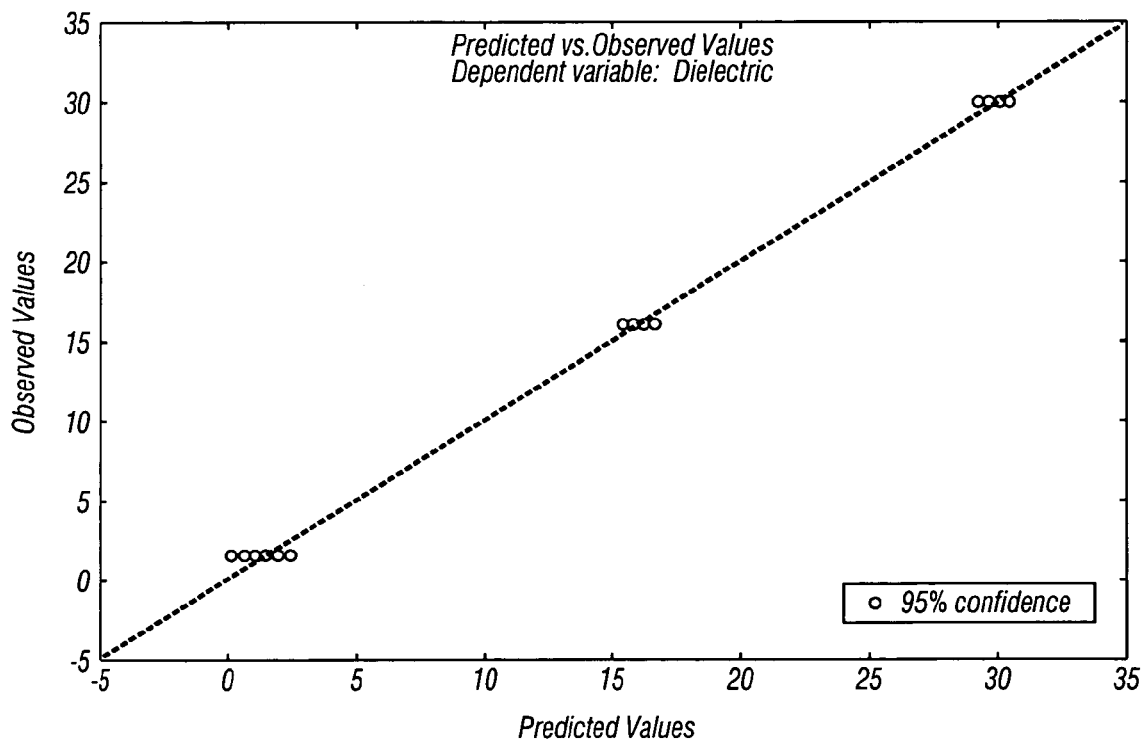
Figure 8C:
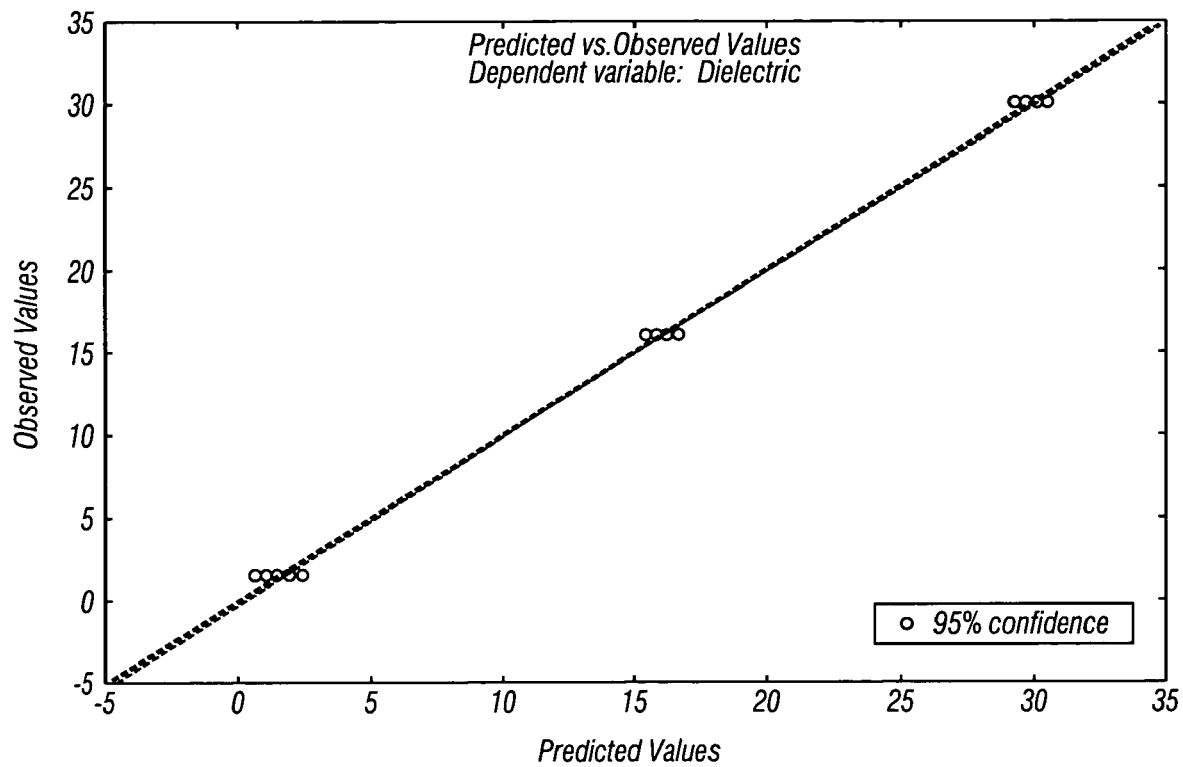
Figure 8D:
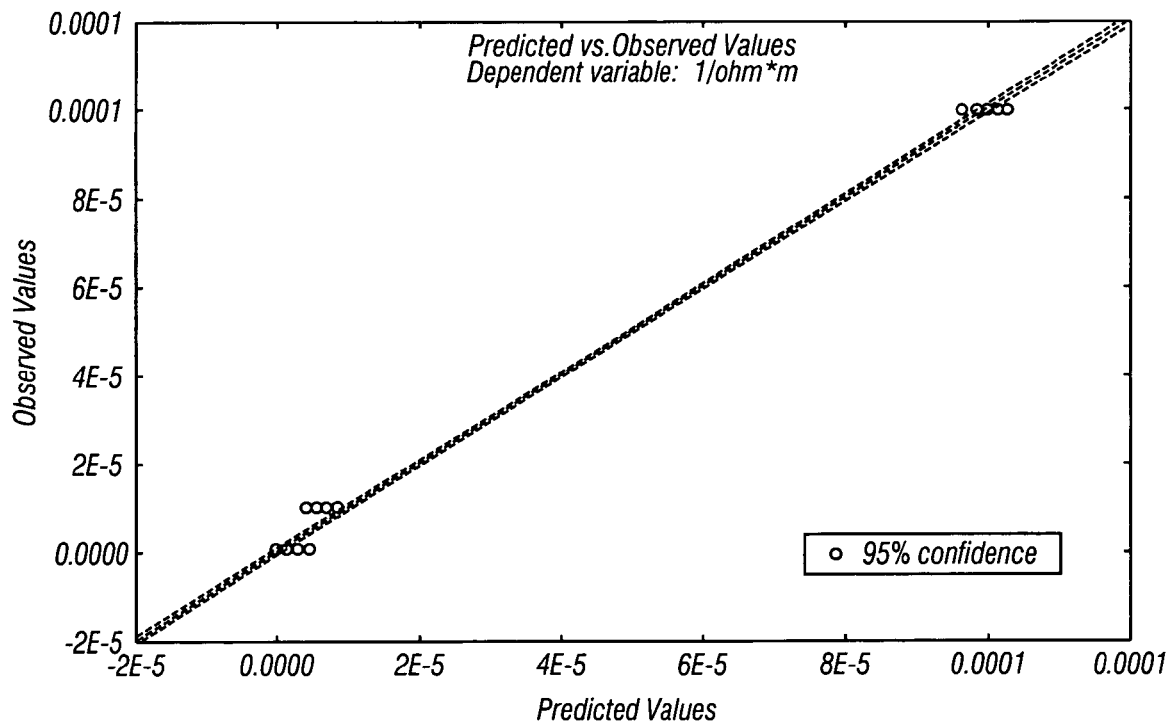

FIG. 5 is an illustration of an example of the present invention mechanical resonator assembly 410 showing a flow line 426 and an associated resonator 411. The resonator 411, in this case a mechanical resonating tuning fork is attached to an actuator and monitoring circuitry 450 by wires 451. The actuator and monitor circuitry 450 is associated with a processor 452. The processor 452 comprises memory, data input output capability and a central processing unit. The actuator and monitor circuitry 450 and associated processor 452 actuate the resonator associated with the fluid and measure the impedance versus frequency spectrum for the resonator associated with the fluid.

If the probe 418 is pulled away from the bore hole wall the fluid entering the tool is well bore fluid rather than formation fluid. Thus, the fluid can come from the formation or from the well bore. The processor performs a function which applies derived chemometric equations to the resonator's measured impedance versus frequency spectrum associated with the fluid to determine the fluid's viscosity, density, dielectric constant, resistivity and other fluid parameters for which chemometric equations are derived. The chemometrically determined fluid parameter values are used directly for an estimation of the fluid's viscosity, density, dielectric constant, resistivity and other fluid parameters. The chemometrically determined fluid parameter values are also used as input to the LM algorithm as an initial estimation of the fluid's viscosity, density, dielectric constant, resistivity and other fluid parameters.

Turning now to FIG. 6. an illustration is shown of exemplary functions performed in part as a computer programmed set of functions performed by the processor 452 in the present invention. In block 610, the present invention performs the function of creating a synthetic data training set for resonator response (impedance versus frequency) when the resonator is immersed in various fluids. This is done in accordance with the principles of experimental design using several values (e.g., high, medium, and low value) for each fluid property (viscosity, resistivity, density and dielectric constant). In block 620 the present invention performs the function of creating chemometric equations that correlate fluid properties to impedance versus frequency for this training set of synthetic data. Examples of chemometric correlations are shown FIGS. 7A-7F (correlations to density and viscosity 702, 704, 706, 708, 710 and 712) and in FIG. 8 (correlations to dielectric constant and conductivity 803, 809, 806 and 808 and variable definitions 810). In block 630 the present invention performs the function of applying these chemometric equations to measured resonator response so as to estimate fluid properties such as viscosity, density, dielectric constant, resistivity and other properties. These fluid parameter values, which are determined by the chemometric equations in block 630, are used directly as the final fluid property values. In block 640, the present invention performs the function of using these chemometric estimates as the starting values for a Levenberg-Marquardt non-linear least-squares fit, which in turn generates the final fluid property values. The LM algorithm function runs on processor 452 and outputs fluid parameter values.

FIGS. 7A-7F and 8A-8E illustrate correlations to a synthetic data set that were prepared using a 3-level experimental design and a theoretical model for a resonator's impedance spectrum as a function of the fluid's density, viscosity, dielectric constant and resistivity. This synthetic data set included all 81 combinations of three levels of four fluid properties, density (0.5, 1.0, and 1.5 g/cc), viscosity (0.5, 2.0, and 3.5 cPs), dielectric constant (1.5, 16, and 30), and resistivity ($10^4$, $10^5$, and $10^6$ ohm-meters). These levels were chosen to provide extremes of these properties that are not likely to be encountered in downhole fluids, thereby insuring that the resulting models are interpolating rather than extrapolating when applied to downhole fluids. One example of a suitable resonator is a small tuning fork, approximately 2 mm×5 mm. This tuning fork resonator inexpensive and has no macroscopically moving parts. The tuning forks can operate at elevated temperature and pressure and enables a more accurate method of determining the characteristic of a downhole fluid, than other known methods.

Figure 9:
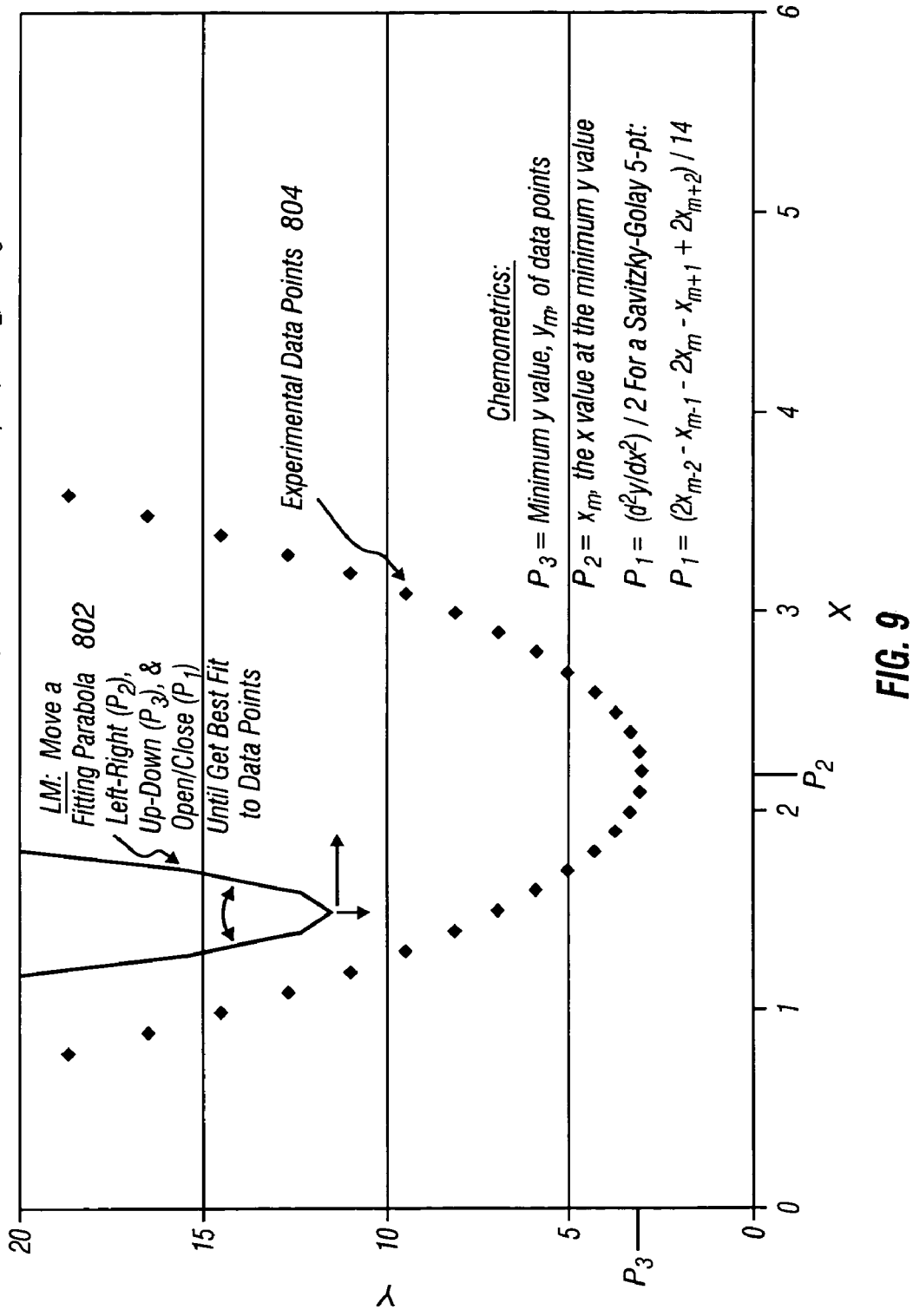
FIG. 9 is a conceptual comparison of the Levenberg-Marquardt non-linear least squares fit method to the chemometrics approach. The two methods can be used alone or in combination, with chemometrics providing the initial guesses for the LM fitting.

FIG. 9 is a conceptual comparison of applying a chemometric model to experimental data instead of performing an iterative LM non-linear least squares fit to the same data to determine the best-fit parameters. In this example, we assume that the experimental data is described by a theoretical model having the form of a parabola, $Y=P_1*(X-P_2)^2+P_3$. The LM method starts with guesses for the three parameters, narrowness of parabola ($P_1$), height above X-axis ($P_2$), and distance of the parabola's axis of symmetry from Y-axis ($P_3$). Then, LM iterates until its corresponding parabolic curve 802 most closely overlays the experimental data points 804.

When a chemometric equation is available, applying it is both quicker and simpler than an iterative approach. In this example, the X and Y values of the lowest experimental data point are $P_2$ and $P_3$, respectively, and $P_1$ simply equals one-half of the second derivative of these data points. Because the data points are evenly spaced along the X-axis, a 5-consecutive-point numerical second derivative can be obtained by standard Savitzky-Golay methods (A. Savitzky and M. Golay, "Smoothing and Differentiation of Data by Simplified Least Squares Procedures," Anal. Chem. vol. 36, No. 8, July, 1964, pp. 1627-1639). Then, $P_1=(2x_{m-2}-x_{m-1}-2x_m-x_{m+1}+2x_{m+2})/14$, where $x_{m-2}$ to $2x_{m+2}$ are five consecutive experimental data points, preferably ones near the minimum of the parabola where experimental error would have the least effect on the calculated value of $P_1$.

Typically one fluid property dominates over the other properties in its influence on a particular feature of the impedance plot of a tuning fork immersed in a fluid. Therefore, we can make rough qualitative assessments of fluid properties from a simple visual inspection of the features of such plots.

Figure 10:
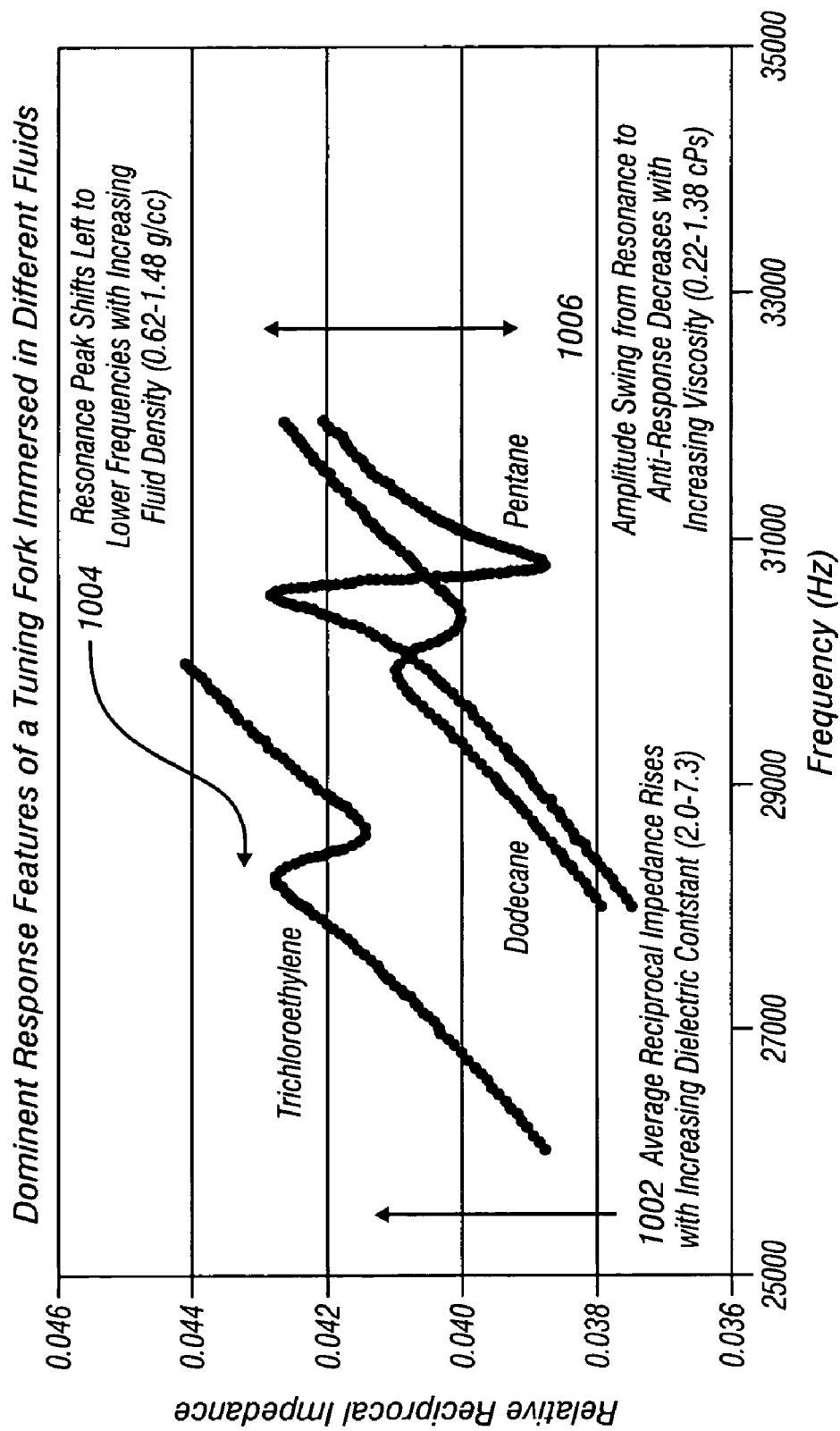
FIG. 10 shows the dominant effects of fluid properties on various features of the impedance plot of a tuning fork immersed in a fluid.

FIG. 10 illustrates these dominant effects. The higher the density of the fluid, the lower the resonant frequency of the fork, so the further left that the resonant peak, 1004, appears. The higher the viscosity of the fluid, the smaller the amplitude, 1006, of the reciprocal impedance swing from the resonance peak to the anti-resonance valley. The higher the dielectric constant or conductivity of the fluid, the more that the average reciprocal impedance, 1002, rises within the same frequency range.

Unfortunately, these are only the dominant effects. Each property of the fluid has an effect on every characteristic feature in the impedance plot. Therefore, to obtain quantitative values for the properties of the fluid, the example of the present invention applies chemometrics and/or a non-linear least squares fit to the impedance data as explained in this invention.

Figure 11:
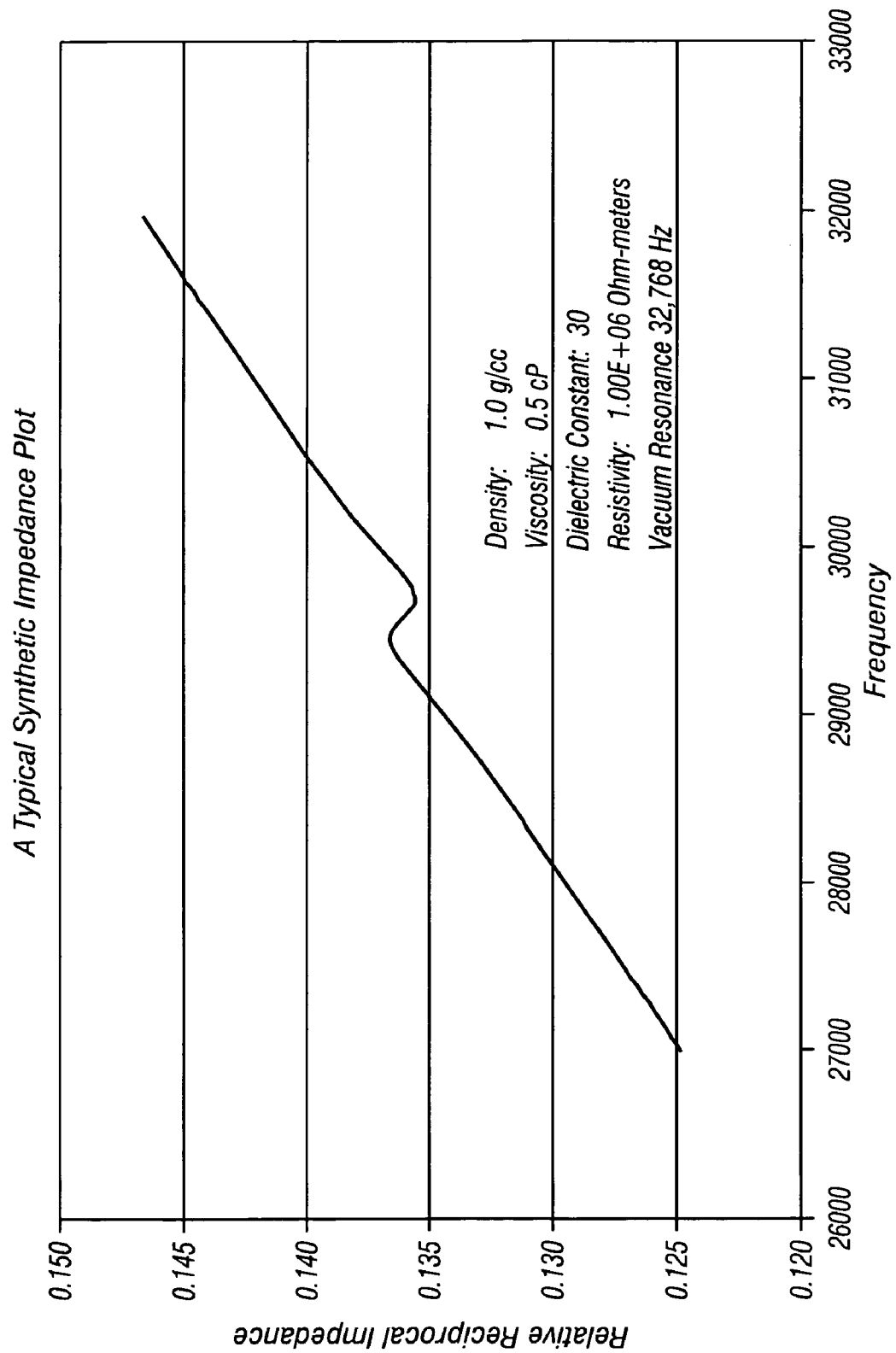
FIG. 11 shows a typical synthetic impedance plot used in this invention with the data plotted every 12.5 Hz.
Figure 12:
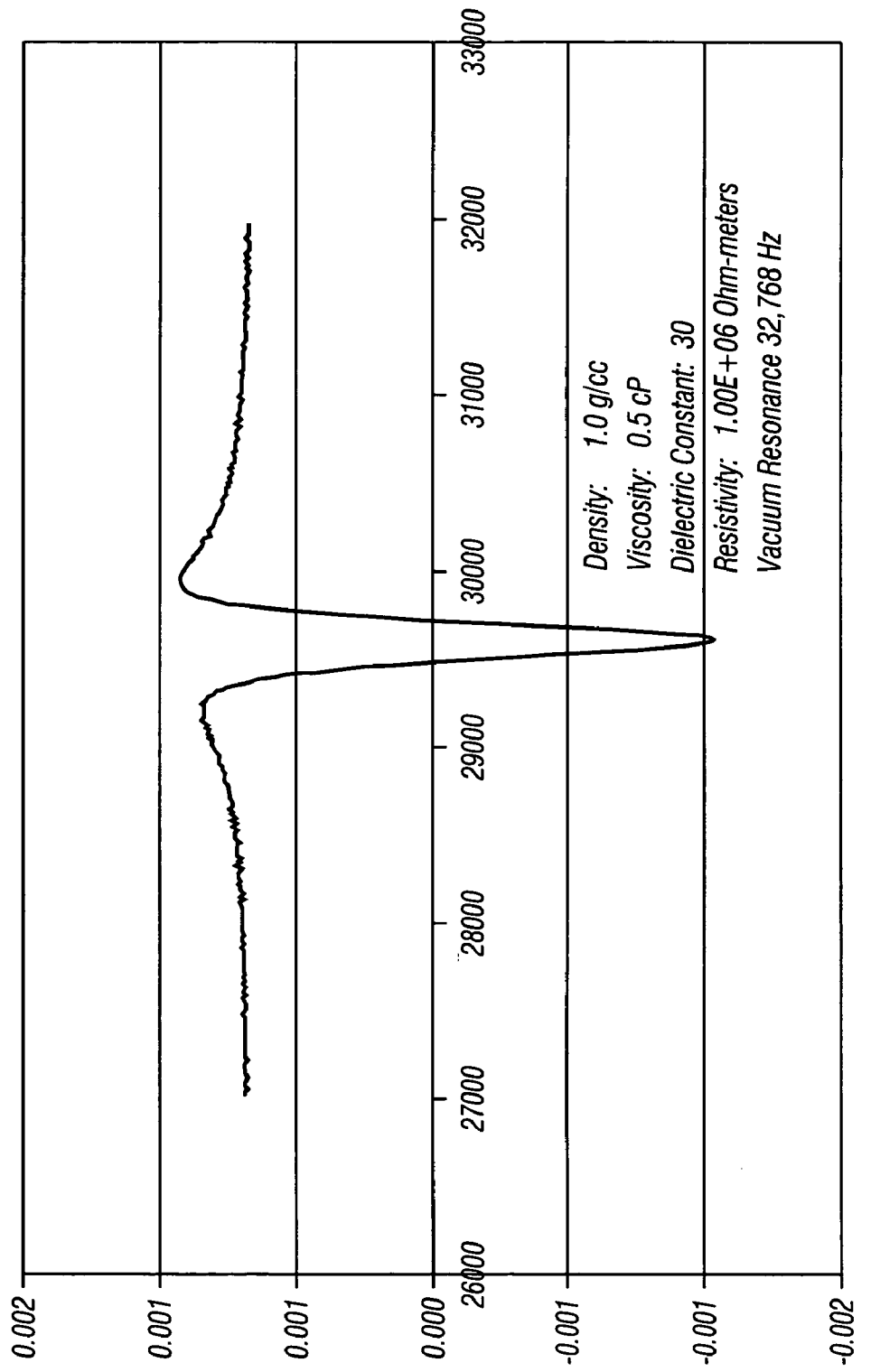
FIG. 12 shows the numerical first derivative of the FIG. 11 curve as calculated by the Savitzky-Golay formula, $(x_{m-2}-8x_{m-1}+8x_{m+1}-x_{m+2})/12$, for every 5 consecutive points, $x_{m-2}$ to $x_{m+2}$. The coefficient for $x_m$ is zero.
Figure 13:
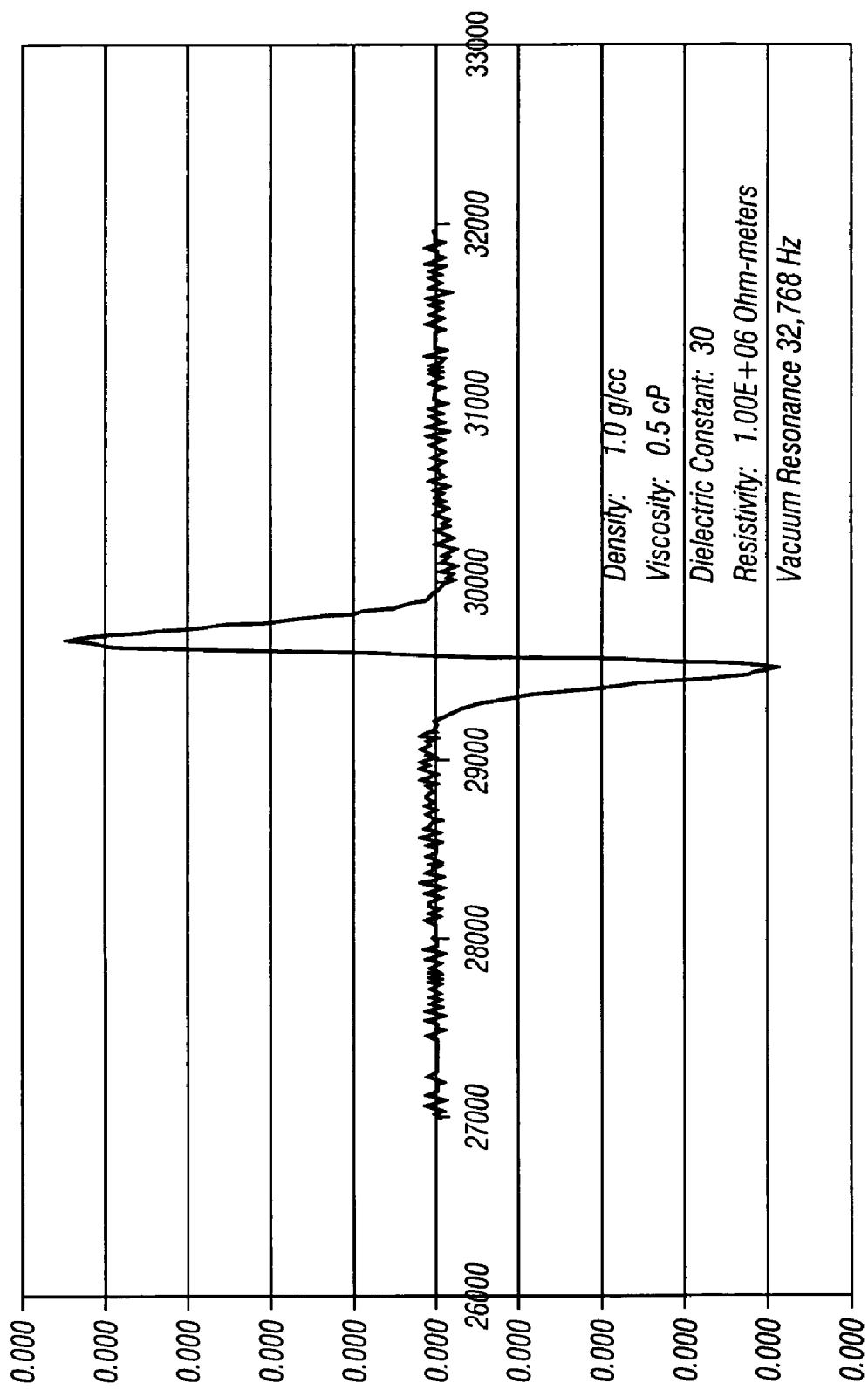
FIG. 13 shows the numerical second derivative of the FIG. 11 curve as calculated by the Savitzky-Golay formula, $(2x_{m-2}-x_{m-1}-2x_m-x_{m+1}+2x_{m+2})/7$, for every 5 consecutive points, $x_{m-2}$ to $x_{m+2}$.

To help the reader visualize the synthetic data described in this invention, FIG. 11 shows a typical synthetic impedance curve 1102 for a tuning fork immersed in a fluid. FIG. 12 shows the first derivative 1202 of the FIG. 11 curve. FIG. 13 shows the second derivative 1302 of the FIG. 11 curve.

The present invention is utilized to provide density, viscosity, dielectric constant, resistivity and other measured, calculated or derived fluid parameter information about a downhole fluid. The tool of the present invention provides the fluid parameter information to a processor or intelligent completion system (ICS) at the surface. The ICS is a system for the remote, intervention less actuation of downhole completion equipment has been developed to support the ongoing need for operators to lower costs and increase or preserve the value of the reservoir. Such a system is described in The Oil and Gas Journal, Oct. 14, 1996. At times called "SmartWells," these completion systems enable oil and gas companies to study and control individual zones without well intervention. This can dramatically lower operating expenditures by reducing downtime. Also, it can allow enhanced hydrocarbon recovery via improved reservoir management. ICSs enable the operator to produce, monitor and control the production of hydrocarbons through remotely operated completion systems. These systems are developed with techniques that allow the well architecture to be reconfigured at will and real-time data to be acquired without any well intervention.

The operator, located at the surface and having access to over ride the processor/ICE 30 may make his own decisions and issue commands concerning well completion based on the measurements provided by the present invention. The present invention may also provide data during production logging to determine the nature of fluid coming through a perforation in the well bore, for example, the water and oil ratio.

The present invention has been described as a method and apparatus operating in an oil rig environment in the example embodiment, however, the present invention may also be embodied as a set of instructions on a computer readable medium, comprising ROM, RAM, CD ROM, Flash or any other computer readable medium, now known or unknown that when executed cause a computer to implement the method of the present invention. An example of an embodiment of the invention has been shown by the above example. This example, however, is for purposes of example only and not intended to limit the scope of the invention, which is defined by the following claims.

What is claimed is:

1. An apparatus for determining the properties of a fluid downhole comprising:
   (a) a resonator in contact with the fluid downhole, wherein the resonator electrical impedance is responsive to properties of the fluid;
   (b) a controller that actuates the resonator;
   (c) a monitor for measuring electrical impedance of the resonator and
   (d) a processor that chemometrically estimates the property of the fluid using the response of the resonator to the actuation.

2. The apparatus of claim 1, wherein the processor correlates a measured resonator response with known fluid property values.

3. The apparatus of claim 1, wherein the property is viscosity.

4. The apparatus of claim 1, wherein the property is density.

5. The property of claim 1, wherein the property is dielectric constant.

6. The apparatus of claim 1, wherein the property is resistivity.

7. The apparatus of claim 1, the processor applies the chemometrically estimated property to a Levenberg-Marquardt (LM) algorithm to determine a fluid parameter value for the fluid.

8. The downhole tool of claim 7, wherein the fluid parameter value comprises a global minimum for the LM algorithm.

9. A method for determining a property of a fluid downhole the method comprising:
   (a) positioning a resonator adjacent to the downhole fluid;
   (b) actuating the resonator;
   (c) measuring the electrical impedance response of the resonator to the actuation; and
   (d) chemometrically estimating a value of a property of the fluid downhole based on the measured response while the fluid is one of (i) being pumped, and (ii) static, wherein the property of the fluid is selected from the list consisting of viscosity, density, dielectric constant and resistivity.

10. The method of claim 9, further comprising: correlating the response with known fluid property values.

11. The apparatus of claim 9, the processor applies the chemometrically estimated property to a Levenberg-Marquardt (LM) algorithm to determine a fluid parameter value for the fluid.

12. The method of claim 11, wherein the fluid parameter value comprises a global minimum for the LM algorithm.

13. A system for determining the properties of a downhole fluid, the system comprising:
(a) a surface controller that lowers a tool deployed in a well bore formed in an adjacent formation, the tool interacting with a down hole fluid;
(b) a resonator in contact with the downhole fluid;
(c) a controller that actuates the resonator; and
(d) a processor that estimates a value of a property for the downhole fluid using an electrical impedance response of the resonator and uses a chemometric equation.

14. The system of claim 13, wherein the processor applies a function applying the resonator response to a chemometric equation to determine the fluid property value.

15. The system of claim 13, wherein the processor uses a function for deriving a chemometric equation from measured resonator response correlated with known fluid property values.

16. The system of claim 13, wherein the parameter value property is viscosity.

17. The system of claim 13, wherein the parameter value property is density.

18. The system of claim 13, wherein the parameter value is dielectric constant.

19. The system of claim 13, wherein the parameter value property is resistivity.

20. The apparatus of claim 13, the processor applies the chemometrically estimated property to a Levenberg-Marquardt (LM) algorithm to determine a fluid parameter value for the fluid.

21. The system of claim 20, wherein the fluid parameter value comprises a global minimum for the LM algorithm.

22. The apparatus of claim 1 wherein the resonator comprises a mechanical resonator.

23. The apparatus of claim 1 wherein the resonator comprises a tuning fork.

24. An apparatus for determining a property of a fluid downhole comprising:
(a) a resonator in direct contact with the fluid downhole;
(b) a controller that actuates the resonator; and
(c) a processor that estimates the property of the fluid using a an electrical impedance response of the resonator to the actuation and uses a chemometric equation.

25. The method of claim 9 further comprising generating creating a synthetic data training set for resonator response.

* * * * *